(12) United States Patent
Biswas et al.

(10) Patent No.: US 8,278,463 B2
(45) Date of Patent: Oct. 2, 2012

(54) PROCESS FOR THE PREPARATION OF PURE DULOXETINE HYDROCHLORIDE

(75) Inventors: Sujoy Biswas, Nadia (IN); Keya Karanjai, Varanasi (IN)

(73) Assignee: Ranbaxy Laboratories Limited, New Delhi (IN)

(*) Notice: Subject to any disclaimer, the term of this patent is extended or adjusted under 35 U.S.C. 154(b) by 496 days.

(21) Appl. No.: 12/418,900

(22) Filed: Apr. 6, 2009

(65) Prior Publication Data
US 2009/0275760 A1    Nov. 5, 2009

(30) Foreign Application Priority Data
Apr. 4, 2008  (IN) .............................. 903/DEL/2008

(51) Int. Cl.
*C07D 333/10* (2006.01)
(52) U.S. Cl. ............................................ 549/75; 549/29
(58) Field of Classification Search ................... 549/29, 549/75
See application file for complete search history.

(56) References Cited

U.S. PATENT DOCUMENTS

| 5,362,886 A | 11/1994 | Berglund |
| 7,534,900 B2 * | 5/2009 | Ini et al. .......................... 549/75 |
| 2006/0194869 A1 | 8/2006 | Ini et al. |

FOREIGN PATENT DOCUMENTS

| IN | 1553/DEL/2006 | 7/2006 |
| IN | 1554/DEL/2006 | 7/2006 |
| WO | WO 2007/038253 | 4/2007 |
| WO | WO 2007/076733 | 7/2007 |
| WO | WO 2007/077580 | 7/2007 |
| WO | WO 2007/105021 | 9/2007 |
| WO | WO 2007/119116 | 10/2007 |
| WO | WO 2007/134168 | 11/2007 |
| WO | WO 2007/148096 | 12/2007 |
| WO | WO 2007/148102 | 12/2007 |
| WO | WO 2007/148103 | 12/2007 |

OTHER PUBLICATIONS

Wheeler, et al., "An Asymmetric Synthesis of Duloxetine Hydrochloride, A Mixed Uptake Inhibitor of Serotonin and Norepinephrine, and Its C-14 Labeled Isotopomers", *Journal of Labelled Compounds and Radiopharmaceuticals*, 36(3), 213-223 (1995).

* cited by examiner

Primary Examiner — Golam M M Shameem

(57) ABSTRACT

The present invention relates to a process for the preparation of pure Duloxetine hydrochloride. The present invention further relates to duloxetine hydrochloride substantially free of residual hydrochloric acid.

4 Claims, No Drawings

PROCESS FOR THE PREPARATION OF PURE DULOXETINE HYDROCHLORIDE

FIELD OF THE INVENTION

The present invention relates to a process for the preparation of pure duloxetine hydrochloride. The present invention further relates to duloxetine hydrochloride substantially free of residual hydrochloric acid.

BACKGROUND OF THE INVENTION

Duloxetine hydrochloride is a selective serotonin and norepinephrine reuptake inhibitor (SSNRI) available in the market for the treatment of major depressive disorder. It is chemically (+)-(S)—N-methyl-γ-(1-naphthyloxy)-2-thiophenepropylamine hydrochloride as represented by Formula I:

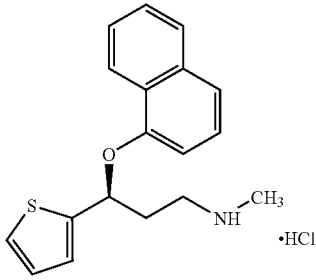

FORMULA I

The processes for the preparation of duloxetine hydrochloride are provided in several prior art references.

U.S. Pat. No. 5,362,886 provides a process for preparing duloxetine hydrochloride, wherein an ethyl acetate solution of duloxetine free base is treated with concentrated hydrochloride acid, followed by further addition of ethyl acetate. The solid so obtained is isolated from the reaction mixture by concentration and subsequent filtration. The solid is then washed with chilled ethyl acetate to obtain duloxetine hydrochloride.

Wheeler, W. J., et al *J. Label. Cpds. Radiopharm.*, 1995, 36, 312 provides a process for preparing duloxetine hydrochloride, wherein an ethyl acetate solution of duloxetine free base is treated with hydrochloric acid in ethyl acetate. The solid so obtained is isolated from the reaction mixture by the addition of ether and subsequent filtration. The solid is then washed with fresh ether and dried to obtain duloxetine hydrochloride. Similar process for preparing duloxetine hydrochloride is also provided in PCT Publication No. WO 2007/077580, wherein the final solid product is washed with ethyl acetate and dried to obtain duloxetine hydrochloride. Our co-pending Indian Patent Application No. 1554/DEL/2006 provides a process for preparing duloxetine hydrochloride, wherein an ethyl acetate solution of duloxetine free base is treated with hydrochloric acid in ethyl acetate to obtain duloxetine hydrochloride, which is further purified by recrystallization from ethanol and diisopropyl ether.

PCT Publication No. WO 2007/076733 provides a process for preparing duloxetine hydrochloride, wherein an ethylmethylketone solution of duloxetine free base is treated with concentrated hydrochloride acid. The duloxetine hydrochloride so obtained is isolated from the reaction mixture by concentration under vacuum. Similar process for preparing duloxetine hydrochloride is also provided in PCT Publication No. WO 2007/038253.

U.S. Patent Application Publication No. 2006/0194869 provides a process for preparing duloxetine hydrochloride, wherein an acetone solution of duloxetine free base is bubbled with hydrogen chloride gas. The solid so obtained is isolated from the reaction mixture by filtration. The solid is washed with acetone and dried in vacuum to obtain duloxetine hydrochloride.

According to prior art methods, duloxetine free base is treated with hydrochloric acid in the presence of ester or ketone solvents. The prior art methods employ hydrochloric acid in concentrated form, in diluted forms with ethyl acetate, or as a gas. The solid obtained is isolated by concentration and/or filtration, which is subsequently washed and dried to obtain duloxetine hydrochloride. Washing is generally carried out to remove the soluble by-products and drying is finally carried out to remove the residual solvents. The present inventors have observed that even after usual washing and drying steps, the finally obtained duloxetine hydrochloride is contaminated with 4-[3-(methylamino)-1-thiophen-2-ylpropyl]naphthalen-1-ol of Formula II in undesirable amounts.

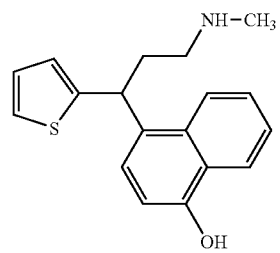

FORMULA II

PCT Publication Nos. WO 2007/105021, WO 2007/119116 and WO 2007/134168 provide methods for preparing and detecting 4-[3-(methylamino)-1-thiophen-2-ylpropyl]naphthalen-1-ol of Formula II in duloxetine hydrochloride. The present inventors have observed that the formation of this compound essentially takes place during the drying process. The present inventors have further observed that the compound of Formula II is formed more than about 80% during drying even if washing is carried out two or three times. Further, the formation of this impurity is observed to be a critical problem when duloxetine hydrochloride is prepared in large scale.

SUMMARY OF THE INVENTION

The present inventors have surprisingly found that the residual hydrochloric acid, which is trapped in solid duloxetine hydrochloride even after washing procedure, rearranges the duloxetine molecule to form the compound of Formula II in undesirable quantities during drying. The content of residual hydrochloric acid is increased when hydrochloric acid is used more than equimolar quantities during the preparation of duloxetine hydrochloride from the free base. The hydrochloric acid is generally used in the processes more than equimolar quantities in order to ensure complete salt formation. However, the present inventors have found that by controlling the pH of the filtrate during filtration and washing procedure, the formation of the compound of Formula II can be minimized. The present inventors have also observed that, when washing is carried out till the pH of the filtrate reaches the range of about 5 to about 6, the duloxetine hydrochloride can be obtained substantially free of the compound of Formula II after drying process.

The present inventors have also found that the use of ethanolic hydrochloric acid for preparing duloxetine hydrochloride also helps in reducing the residual hydrochloric acid content and thus, minimizes the formation of compound of Formula II while drying. In addition, the ethanolic hydrochloric acid can be prepared in such a way that it contains about 27% w/w of hydrochloric acid when compared to ethyl acetate—hydrochloric acid solutions, which can practically contain only up to about 8% w/w of hydrochloric acid. Thus, the use of ethanolic hydrochloric acid tremendously reduces the quantity of solvent which needs to be used for preparing duloxetine hydrochloride. Therefore, the present invention provides an efficient process for preparing duloxetine hydrochloride with improved purity and yield, and the present process is also suitable to produce pure duloxetine hydrochloride in industrial scale in more economic way.

DETAILED DESCRIPTION OF THE INVENTION

A first aspect of the present invention provides duloxetine hydrochloride substantially free of residual hydrochloric acid. The duloxetine hydrochloride substantially free of residual hydrochloric acid is characterized by having chloride content of about 10.7% w/w or less. The duloxetine hydrochloride substantially free of residual hydrochloric acid preferably has a chloride content of about 10.5 to about 10.6% w/w.

A second aspect of the present invention provides a process for the preparation of pure duloxetine hydrochloride, wherein the process comprises,
 a) treating duloxetine free base with hydrochloric acid in the presence of an organic solvent to obtain duloxetine hydrochloride,
 b) isolating the duloxetine hydrochloride from the reaction mixture of step a)
 c) washing the isolated duloxetine hydrochloride with an organic solvent till the pH of the filtrate attains the range of about 5 to about 6, and
 d) drying the duloxetine hydrochloride obtained in step c) to obtain pure duloxetine hydrochloride.

Duloxetine free base may be prepared according to the methods provided in Wheeler, W. J., et al *J. Label. Cpds. Radiopharm.*, 1995, 36, 312, U.S. Pat. No. 5,362,886 or our co-pending Indian Patent Applications Nos. 1553/DEL/2006 and 1554/DEL/2006. The duloxetine free base used as starting material may be present in solid form or in oil form. The duloxetine free base is dissolved in an organic solvent. The organic solvent may be an ester, a ketone, an alcohol or a mixture thereof. The organic solvent may be, for example, ethyl acetate, ethanol, methanol, acetone or a mixture thereof. The duloxetine free base dissolved in the organic solvent is treated with hydrochloric acid. The hydrochloric acid may be used in concentrated form, or in diluted form with aqueous or non-aqueous solvents. The hydrochloric acid may also be used as a gas. The hydrochloric acid is used in equimolar quantities with respect to the molar quantity of duloxetine or in slight excess, for example, about 1.2 to about 1.5 molar equivalents. The formation of duloxetine hydrochloride may be facilitated by stirring the reaction mixture. The stirring may be carried out at the temperature of about 0° to about 30° C. The duloxetine hydrochloride is isolated from the reaction mixture by filtration, concentration or distillation. The duloxetine hydrochloride so obtained is washed with an organic solvent. The organic solvent may be an ester or a ketone, for example, ethyl acetate or acetone. The washing is carried out till the pH of the filtrate attains the range of about 5 to about 6. The washing may be performed by passing the organic solvent through duloxetine hydrochloride, by slurrying the duloxetine hydrochloride in the organic solvent or by a combination thereof. When the pH of the filtrate resulting from washing attains the range of about 5 to about 6, the duloxetine hydrochloride is subjected to drying. The drying may be carried out by the methods known in the art. The drying may be carried out, for example, under vacuum to obtain pure duloxetine hydrochloride. The pure duloxetine hydrochloride so obtained is substantially free of 4-[3-(methylamino)-1-thiophen-2-ylpropyl]naphthalen-1-ol of Formula II and residual hydrochloric acid. The duloxetine hydrochloride so obtained contains 4-[3-(methylamino)-1-thiophen-2-ylpropyl]naphthalen-1-ol of Formula II of about 0.1% w/w or less, preferably about 0.05% w/w or less, and more preferably about 0.01% w/w or less. The duloxetine hydrochloride so obtained has a chloride content of about 10.7% w/w or less, preferably about 10.5 to about 10.6% w/w.

A third aspect of the present invention provides a process for the preparation of duloxetine hydrochloride, wherein the process comprises,
 a) treating duloxetine free base with ethanolic hydrochloric acid in the presence of an organic solvent to obtain duloxetine hydrochloride, and
 b) isolating the duloxetine hydrochloride from the reaction mixture thereof.

Duloxetine free base can be prepared according to the methods provided in Wheeler, W. J., et al *J. Label. Cpds. Radiopharm.*, 1995, 36, 312, U.S. Pat. No. 5,362,886 or our co-pending Indian Patent Application Nos. 1553/DEL/2006 and 1554/DEL/2006. The duloxetine free base used as starting material may be present in solid form or in oil form. The duloxetine free base is dissolved in an organic solvent. The organic solvent may be an ester, a ketone, an alcohol or mixtures thereof. The organic solvent may be, for example, ethyl acetate, ethanol, methanol, acetone or a mixture thereof. The duloxetine free base dissolved in the organic solvent is treated with ethanolic hydrochloric acid. The ethanolic hydrochloric acid may be prepared by contacting ethanol with hydrochloric acid. The ethanolic hydrochloric acid contains about 10% to about 27% w/w of hydrochloric acid. The formation of duloxetine hydrochloride may be facilitated by stirring the reaction mixture. The stirring may be carried out at the temperature of about 0° to about 30° C. The duloxetine hydrochloride may be isolated from the reaction mixture by filtration, concentration, distillation, drying or a combination thereof. The duloxetine hydrochloride so obtained contains 4-[3-(methylamino)-1-thiophen-2-ylpropyl]naphthalen-1-ol of Formula II of about 3.0% w/w or less, for example, about 2.5% w/w or less. The duloxetine hydrochloride so obtained may be further purified by crystallization, washing, and/or drying.

While the present invention has been described in terms of its specific embodiments, certain modifications and equivalents will be apparent to those skilled in the art and are intended to be included within the scope of the present invention.

EXAMPLES

Example 1

Preparation of Duloxetine Hydrochloride and Isolation of 4-[3-(methylamino)-1-thiophen-2-ylpropyl]naphthalen-1-ol A) Preparation of Duloxetine Hydrochloride:

Sodium hydroxide solution (30% w/v; 100 ml) was added to a stirred suspension of duloxetine maleate (105 g; 0.254 mole) in a mixture of toluene (1.05 L) and deionised water (1.05 L) at about 25° C. to attain a pH of 11 to 12. The mixture was stirred for 10 minutes. Toluene layer was separated and aqueous layer was subsequently extracted with toluene (525 ml). The combined toluene layer was washed with deionised water (2×525 ml) and concentrated under vacuum to obtain duloxetine free base as an oily mass. The duloxetine free base so obtained was stirred in ethyl acetate (472.5 ml) and ethyl acetate—hydrochloric acid solution (140 ml; 0.276 mole; 8% w/w; 1.1 mole equivalent) was added to the stirred solution at 15° to 20° C. The mixture was stirred at 15° to 20° C. for 30 minutes, at 20° to 25° C. for 2 hours and subsequently at 5° to 10° C. for 2 hours. The solid was filtered, washed with ethyl acetate (2×105 ml) and dried under vacuum at 40° to 45° C. to obtain the title compound as a brownish solid.

Yield: 68 g
Purity (HPLC): 11.25% w/w
4-[3-(Methylamino)-1-thiophen-2-ylpropyl]naphthalen-1-ol: 81.86% w/w B) Isolation of 4-[3-(methylamino)-1-thiophen-2-ylpropyl]naphthalen-1-ol:

The duloxetine hydrochloride (5 g) obtained in step A was treated with 1 N sodium hydroxide (0.72 g; 18 ml) and extracted with toluene (50 ml). The toluene layer was evaporated to obtain the free base of duloxetine (4.4 g). The free base of duloxetine was loaded on a silica gel column (dry slurry with 10 g of silica gel) with dichloromethane. The elution was started with 0.5% v/v of methanol in dichloromethane and the free base of duloxetine was eluted with 1% v/v methanol in dichloromethane, and the eluted fractions were concentrated under vacuum to obtain the free base of duloxetine. The impurity of Formula II was eluted with 10% v/v methanol in dichloromethane and the eluted fractions were concentrated under vacuum to obtain the title compound.

Yield:
Duloxetine free base: 0.4 g
4-[3-(methylamino)-1-thiophen-2-ylpropyl]naphthalen-1-ol: 2.5 g
4-[3-(methylamino)-1-thiophen-2-ylpropyl]naphthalen-1-ol: $^1$H NMR (CD$_3$OD) δ (ppm): 8.23 (brd, 1H), 8.06 (d, J=7.8 Hz, 1H), 7.45-7.40 (m, 2H), 7.31 (d, J=7.5 Hz, 1H), 7.14 (m, 1H), 6.88 (m, 2H), 6.79 (d, J=7.8 Hz, 1H), 4.96 (m, 1H), 2.58 (m, 2H), 2.40 (m, 2H), 3.03 (s, 3H).

Example 2

Preparation of Pure Duloxetine Hydrochloride

Sodium hydroxide solution (30% w/v; 150 ml) was added to a stirred suspension of duloxetine maleate (200 g, 0.484 mole) in a mixture of toluene (2.0 L) and deionised water (2.0 L) at about 25° C. to attain a pH of 11 to 12. The mixture was stirred for 10 minutes. Toluene layer was separated and aqueous layer was extracted with toluene (1.0 L). The combined toluene layer was washed with deionised water (2×1.0 L) and concentrated under vacuum to obtain duloxetine free base as an oily mass. The duloxetine free base so obtained was stirred in ethyl acetate (1.0 L) and ethanolic hydrochloric acid (65.46 g; 0.484 mole; 27% w/w; 1.0 mole equivalent) was added to the stirred solution at 15° to 20° C. The mixture was stirred at 15° to 20° C. for 30 minutes, at 20° to 25° C. for 2 hours and subsequently at 5° to 10° C. for 2 hours. The solid was filtered and subjected to running wash with ethyl acetate (1×200 ml) followed by slurry wash with ethyl acetate (2×400 ml) till the pH of the filtrate attains the range of 5 to 6. The solid so obtained was dried under vacuum at 40° to 45° C. to obtain the title compound as an off-white solid.

Yield: 150 g
HPLC Purity: 99.9% w/w
Impurity of Formula II: Not detectable
Chloride content: 10.56-10.60% (Theoretical content: 10.63%)

Example 3

Preparation of Duloxetine Hydrochloride

Sodium hydroxide solution (30% w/v; 15.5 ml) was added to a stirred suspension of duloxetine maleate (20 g, 0.0484 mole) in a mixture of toluene (200 ml) and deionised water (200 ml) at 15° to 20° C. to attain a pH of 12. The mixture was stirred for 10 minutes. Toluene layer was separated and aqueous layer was extracted with toluene (100 ml). The combined toluene layer was washed with deionised water (2×100 ml) and concentrated under vacuum to obtain duloxetine free base as an oily mass. The duloxetine free base so obtained was stirred in ethyl acetate (140 ml) and ethanolic hydrochloric acid (8.52 g; 0.063 mole; 27% w/w; 1.3 mole equivalent) at 10° to 15° C. The mixture was stirred at 10° to 15° C. for 30 minutes and subsequently at 20° to 25° C. for 3 hours. The reaction mixture was divided into two parts namely Part A and Part B.

The precipitated solid from Part A was filtered and dried under vacuum at 40° to 45° C. to provide the title compound as an off-white solid.

The precipitated solid from Part B was filtered and subjected to slurry wash with ethyl acetate (2×10 ml) till the pH of the filtrate attains the range of 5 to 6. The solid so obtained was dried under vacuum at 40° to 45° C. to obtain the title compound as an off-white solid.

| DULOXETINE HYDROCHLORIDE | METHOD | HPLC (% w/w) | |
|---|---|---|---|
| | | PURITY | IMPURITY OF FORMULA II |
| PART A | Without washing | 93.46 | 2.5 |
| PART B | Washing the filtrate till the pH of the filtrate attains the range of 5 to 6 | 99.82 | 0.04 |

Example 4

Preparation of Duloxetine Hydrochloride

Sodium hydroxide solution (30% w/v; 15.5 ml) was added to a stirred suspension of duloxetine maleate (20 g, 0.0484 mole) in a mixture of toluene (200 ml) and deionised water (200 ml) at 15° to 20° C. to attain a pH of 12. The mixture was stirred for 10 minutes. Toluene layer was separated and aqueous layer was extracted with toluene (100 ml). The combined toluene layer was washed with deionised water (2×100 ml) and concentrated under vacuum to obtain duloxetine free base as an oily mass. The duloxetine free base so obtained was stirred in ethyl acetate (140 ml) and ethanolic hydrochloric acid (6.518 g; 0.0484 mole; 27% w/w; 1.0 mole equivalent) at 10° to 15° C. The mixture was stirred at 10° to 15° C. for 30 minutes and subsequently at 20° to 25° C. for 3 hours. The reaction mixture was divided into two parts namely Part A and Part B.

The precipitated solid from Part A was filtered and dried under vacuum at 40° to 45° C. to provide the title compound as an off-white solid.

The precipitated solid from Part B was filtered and subjected to slurry wash with ethyl acetate (2×10 ml) till the pH of the filtrate attains the range of 5 to 6. The solid so obtained was dried under vacuum at 40° to 45° C. to obtain the title compound as an off-white solid.

| DULOXETINE HYDRO-CHLORIDE | METHOD | HPLC (% w/w) PURITY | IMPURITY OF FORMULA II |
|---|---|---|---|
| PART A | Without washing | 98.72 | 0.31 |
| PART B | Washing the filtrate till the pH of the filtrate attains the range of 5 to 6 | 99.70 | Not Detectable |

Example 5

Preparation of Duloxetine Hydrochloride

Ethyl acetate—hydrochloric acid solution (1.0 ml; 1.66 mmole; 8% w/w; 0.5 mole equivalent) was added to a stirred suspension of duloxetine hydrochloride (1.0 g, 2.99 mmole) in ethyl acetate (5 ml) at about 25° C. The mixture was stirred at the same temperature for 45 minutes. The reaction mixture was divided into two parts namely Part A and Part B.

The solid from part A was filtered and dried under vacuum at 40° to 45° C. to obtain the title compound as an off-white solid.

The solid from Part B was filtered and subjected to slurry wash with ethyl acetate (2×1.0 ml) till the pH of the filtrate attains the range of 5 to 6. The solid so obtained was dried under vacuum at 40° to 45° C. to obtain the title compound as an off-white solid.

| DULOXETINE HYDRO-CHLORIDE | METHOD | HPLC (% w/w) PURITY | IMPURITY OF FORMULA II |
|---|---|---|---|
| PART A | Without washing | 0.06 | 88.22 |
| PART B | Washing the filtrate till the pH of the filtrate attains the range of 5 to 6 | 99.85 | Not Detectable |

We claim:

1. A process for the preparation of pure duloxetine hydrochloride, comprising the steps of
   a) treating duloxetine free base with hydrochloric acid in the presence of an organic solvent to obtain duloxetine hydrochloride,
   b) isolating the duloxetine hydrochloride from the reaction mixture of step a),
   c) washing the isolated duloxetine hydrochloride from step b) with an organic solvent till the pH of the filtrate is in the range of about 5 to about 6, and
   d) drying the duloxetine hydrochloride obtained in step c) to obtain pure duloxetine hydrochloride,
wherein the pure duloxetine hydrochloride obtained in step d) has a chloride content of not more than 10.7% w/w.

2. A process according to claim 1, wherein the hydrochloric acid is used in equimolar quantities with respect to the molar quantity of duloxetine or in slight excess.

3. A process according to claim 1, wherein the washing is performed by passing the organic solvent through duloxetine hydrochloride, by slurrying the duloxetine hydrochloride in the organic solvent or by a combination thereof.

4. A process according to claim 1, wherein the pure duloxetine hydrochloride obtained in step d) contains 4-[3-(methylamino)-1-thiophen-2-ylpropyl]naphthalen-1-ol of Formula II of about 0.1% w/w or less

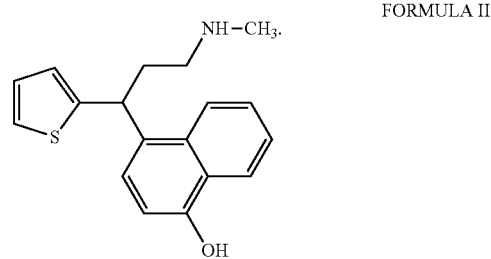

FORMULA II

* * * * *